(12) United States Patent
Gordon et al.

(10) Patent No.: US 7,560,581 B2
(45) Date of Patent: Jul. 14, 2009

(54) VAPOR DEPOSITION OF TUNGSTEN NITRIDE

(75) Inventors: Roy G. Gordon, Cambridge, MA (US); Seigi Suh, Cary, NC (US); Jill Becker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 447 days.

(21) Appl. No.: 10/520,456

(22) PCT Filed: Jul. 9, 2003

(86) PCT No.: PCT/US03/21281

§ 371 (c)(1),
(2), (4) Date: Oct. 19, 2005

(87) PCT Pub. No.: WO2004/007796

PCT Pub. Date: Jan. 22, 2004

(65) Prior Publication Data

US 2006/0125099 A1    Jun. 15, 2006

Related U.S. Application Data

(60) Provisional application No. 60/395,572, filed on Jul. 12, 2002.

(51) Int. Cl.
- *C07F 11/00* (2006.01)
- *C23C 16/34* (2006.01)
- *H01L 21/44* (2006.01)

(52) U.S. Cl. .................. 556/63; 257/761; 257/763; 427/255.393; 427/255.394; 427/593; 438/681; 438/685

(58) Field of Classification Search .......... 556/57, 556/63; 427/255.12, 394, 249.18, 255.394, 427/593, 255.393; 257/763, 761; 438/681, 438/685
See application file for complete search history.

(56) References Cited

U.S. PATENT DOCUMENTS 6,114,242 A * 9/2000 Sun et al. ................. 438/687
6,238,734 B1 * 5/2001 Senzaki et al. ............ 427/226
6,359,160 B1 3/2002 Sun et al.
6,969,539 B2 * 11/2005 Gordon et al. ......... 427/255.29

2001/0002280 A1  5/2001  Sneh
2001/0041250 A1  11/2001 Haukka et al.
2001/0054730 A1  12/2001 Kim et al.

FOREIGN PATENT DOCUMENTS

| EP | 1067595 A | 1/2001 |
| JP | 2002093804 A2 | 3/2002 |
| WO | WO-01/27347 A | 4/2001 |
| WO | WO-02/27063 A | 4/2002 |

OTHER PUBLICATIONS

Becker, J. S. et al., "Diffusion Barrier Properties of Tungsten Nitride Films Grown by Atomic Layer Deposition From Bis (Tert-Butylimido) Bis (Dimethylamido) Tungsten and Ammonia" Applied Physics Letters, American Institute of Physics, New York, US, vol. 82, No. 14, Apr. 7, 2003, pp. 2239-2241.

Chuang, Shiow-Huey and Choi, Yi-Hsuan. "Growth of Ternary WC$_x$N$_y$ Thin Films from a Single-source Precursor, W(N$^t$Bu)$_2$ (NEt$_2$)$_2$" J. Chin. Chem. Soc., vol. 53, No. 6, 2006 (1391- 1395).

European Office Action, European Patent Application No. 03 764 377.2, dated Sep. 19, 2006 (6 pages).

Jones, Anthony et al. "MOCVD and ALK of High-κ Dielectric Oxides Using Alkoxide Precursors" Chem. Vap. Deposition, 2006 (12) 83-98.

Nugent, William A. and Harlow, Richard L. "Some bis(tert-butylimido) complexes of the Group 6 Transition Metals and a Related Alkylamido Derivative." Inorganic Chemistry, vol. 19, No. 3, 1980 (777-779).

Sundermeyer, Jorg. 'Neue Organometall-Imide des Molybdans und Wolframs—die direkte Einfuhrung der Cyclopentadienyl-Gruppe durch Maskierung der hohen Oxidationsstufe' Chem. Ber. 124(1991) 1977-1979 (English Abstract Attached.).

* cited by examiner

*Primary Examiner*—Shean C Wu
(74) *Attorney, Agent, or Firm*—Wilmer Cutler Pickering Hale & Dorr LLP

(57) ABSTRACT

Tungsten nitride films were deposited on heated substrates by the reaction of vapors of tungsten bis(alkylimide)bis(dialkylamide) and a Lewis base or a hydrogen plasma. For example, vapors of tungsten bis(tert-butylimide)bis(dimethylamide) and ammonia gas supplied in alternate doses to surfaces heated to 300° C. produced coatings of tungsten nitride having very uniform thickness and excellent step coverage in holes with aspect ratios up to at least 40:1. The films are metallic and good electrical conductors. Suitable applications in microelectronics include barriers to the diffusion of copper and electrodes for capacitors. Similar processes deposit molybdenum nitride, which is suitable for layers alternating with silicon in X-ray mirrors.

31 Claims, 3 Drawing Sheets

VAPOR DEPOSITION OF TUNGSTEN NITRIDE

BACKGROUND OF THE INVENTION

1. Field of the Invention

This invention relates to materials and processes for deposition of thin films on solid substrates. In particular, this invention relates to materials and processes for deposition of tungsten-containing thin films on solid substrates. This invention also relates to methods and materials for making electrically conducting, conformally deposited films for fabrication of devices in the areas of microelectronics.

2. Description of the Related Art

Tungsten nitride, $WN_x$, is considered to be a good barrier against diffusion of copper in microelectronic circuits. $WN_x$ can also be used in electrodes for thin-film capacitors and field-effect transistors. $WN_x$ has been made by reactive sputtering, but the uniformity of film thickness inside narrow features ("step coverage") is not expected to be adequate for use in future microelectronic devices having narrow features with high aspect ratios.

Atomic layer deposition (also known as atomic layer epitaxy) is a process for depositing thin layers of solid materials from two vapor precursors. The surface of a substrate onto which a film is to be deposited is exposed to a dose of vapor from one precursor. Then any excess unreacted vapor from that precursor is pumped away. Next, a vapor dose of the second precursor is brought to the surface and allowed to react. This cycle of steps can be repeated to build up thicker films. Typically, each precursor contributes a portion of the atoms to the deposited film. One particularly important aspect of this process is that the ALD reactions are self-limiting, in that only a certain maximum thickness can form in each cycle, after which no further deposition occurs during that cycle, even if excess reactant is available. Because of this self-limiting character, ALD reactions produce coatings with highly uniform thicknesses. Uniformity of ALD film thickness extends not only over flat substrate surfaces, but also into very narrow holes and trenches. This ability of ALD to make conformal films is called "excellent step coverage."

Coatings of $WN_x$ made by ALD from $WF_6$ and $NH_3$ have good step coverage. A disadvantage of this process is that $WF_6$ and/or its reaction byproduct, HF, can attack substrates made of Si or $SiO_2$. This reaction can also generate unwanted particles of ammonium fluoride byproduct that may cause defects in a semiconductor product. Also, this process can leave the $WN_x$ surface with a fluorine residue that may impede adhesion of copper to the surface. In particular, adhesion of Cu deposited by CVD is often considered to be poor in part because of fluorine contamination at the interface between the tungsten nitride and the copper. Loss of adhesion can cause severe loss of yield in manufacturing or reliability problems during operation of a semiconductor device.

Molybdenum nitride layers may be used along with alternating layers of silicon to make mirrors for X-rays. ALD would be an ideal method for depositing the $MoN_x$ and silicon layers with the required highly uniform thicknesses needed in an X-ray mirror.

SUMMARY OF THE INVENTION

The present invention provides a highly efficient process for depositing conformal coatings, particularly those containing tungsten, on solid substrates. These coatings comprise tungsten, nitrogen, and optionally, may contain oxygen, silicon, carbon and/or hydrogen, and relatively small amounts of other elements. As used herein, the coatings of the present invention are referred to as "tungsten nitride." Tungsten nitride layers with extremely uniform thicknesses and/or tungsten nitride coatings with extremely smooth surfaces are obtained.

One aspect of the present invention is a process for depositing a thin film on the surface of a substrate by a sequential process including one or more cycles, wherein at least one cycle comprises:

(a) exposing the substrate to a vapor of a first material containing at least two elements of the thin film, wherein at least a portion of the first material's vapor adsorbs on the surface of the substrate by a self-limiting process;

(b) removing un-adsorbed vapor of the first material from the vicinity of the substrate;

(c) exposing the substrate to the vapor of a second material that activates the surface so that the surface is prepared to react with additional quantities of said first material; and (d) removing residual vapor of the second material from the vicinity of the substrate.

In one aspect of the invention vapors of bis(alkylamido)bis(dialkylamido) tungsten(VI) are reacted with a Lewis base, such as ammonia or pyridine, on the heated surface of a substrate to form coatings of tungsten nitride. In other embodiments, the tungsten nitride precursor vapor is exposed to an activating plasma.

In at least some embodiments, tungsten compounds have the general formula 1, in which $R''$ represents alkyl groups, fluoroalkyl groups or alkyl groups substituted with other atoms or groups, preferably selected to enhance the volatility of the compound, where $R_n$ is any one of $R^1$ through $R^6$. The $R''$ may be the same or different from each other.

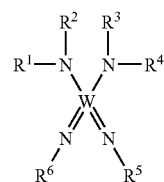

1

In one or more embodiments corresponding to formula 1, the alkyl groups $R^5$ and $R^6$ have a tertiary carbon attached to the imido nitrogen. In one or more embodiments, the compounds have the general structure 2:

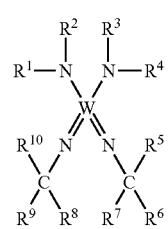

2

This structure is believed to facilitate deposition of films with low carbon content because of the facile beta-hydrogen elimination reactions for alkyl groups with tertiary carbon.

In at least some embodiments methyl groups are selected for all the $R''$ in the general formula 2 given above, obtaining the compound bis(tert-tylimido)bis(dimethylamido) tungsten(VI) having formula 3:

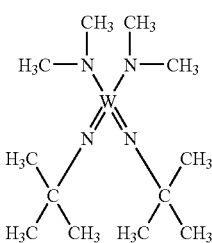

In one or more embodiments of the present invention, the compound is obtained by selecting in formula 2 $R^1$, $R^4$, $R^5$, $R^6$, $R^7$, $R^8$, $R^9$ and $R^{10}$ to be methyl groups, and $R^2$ and $R^3$ to be ethyl groups, to obtain bis(ethylmethylamido)bis(tert-butylimido)tungsten(VI) having formula 4:

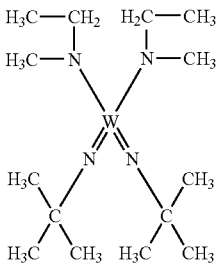

Another compound of the invention is obtained by selecting in formula 1 the groups $R^1$, $R^2$, $R^3$ and $R^4$ to be methyl groups, and $R^5$ and $R^6$ to be isopropyl groups, to obtain bis(dimethylamido)bis(isopropylimido)tungsten(VI) having formula 5:

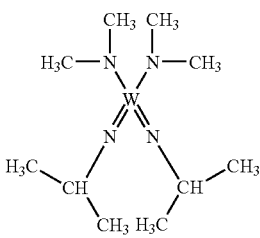

In the foregoing compounds, it is also understood that two or more alkyl groups may be linked to form cyclic compounds, and that the groups may contain some degree of unsaturation, e.g., aryl, alkenyl or alkynyl groups.

In one or more embodiments of the present invention, tungsten nitride films are deposited. The films are deposited under conditions that produce good adhesion between the deposited tungsten nitride film and a substrate onto which it is deposited.

In one or more embodiments strongly adherent films are deposited on top of the tungsten nitride films of the invention. In particular, an adherent copper layer can be deposited on the tungsten nitride layer.

In one or more embodiments, vapor deposition of highly uniform tungsten nitride films is accomplished over a range of conditions such as concentrations of reactants and position of the substrate inside the reactor. In one or more embodiments of the present invention, substrates are coated at relatively low temperatures, e.g., from about 200° C. to 400° C.

The method of the present invention also provides conformal coatings of tungsten nitride over substrates with narrow holes, trenches or other structures. This ability is commonly known as "good step coverage." Tungsten nitride coatings that are substantially free of pinholes or other mechanical defects can also be prepared. Coatings may also be placed on powders or wires, or around and within complicated mechanical structures. The coating can be used in an electrical capacitor or as a barrier to diffusion of metals in microelectronic devices.

The tungsten source is a non-corrosive liquid at room temperature, and the process for atomic layer deposition proceeds without etching or damaging structures (mainly because HF is not a byproduct of the deposition process). Thus, the uniform tungsten nitride films are deposited without fluorine impurity in the film and without toxic fluorine components in the precursor or in the effluent from the process.

In one or more embodiments, an electrically conducting film is provided that is a good barrier to diffusion of copper. The present invention includes a process for depositing electrically conductive tungsten nitride for use as a barrier against diffusion of copper in microelectronic devices, having useful mechanical properties as hard coatings, or useful as protection against diffusion, oxidation or corrosion.

Molybdenum nitride, $MoN_x$, can be deposited by use of analogous compounds with molybdenum in place of tungsten.

BRIEF DESCRIPTION OF THE DRAWINGS

The foregoing and various other aspects, features, and advantages of the present invention, as well as the invention itself, may be more fully appreciated with reference to the following detailed description of the invention when considered in connection with the following drawings. The drawings are presented for the purpose of illustration only and are not intended to be limiting of the invention, in which.

DETAILED DESCRIPTION OF THE INVENTION

Figure 1:
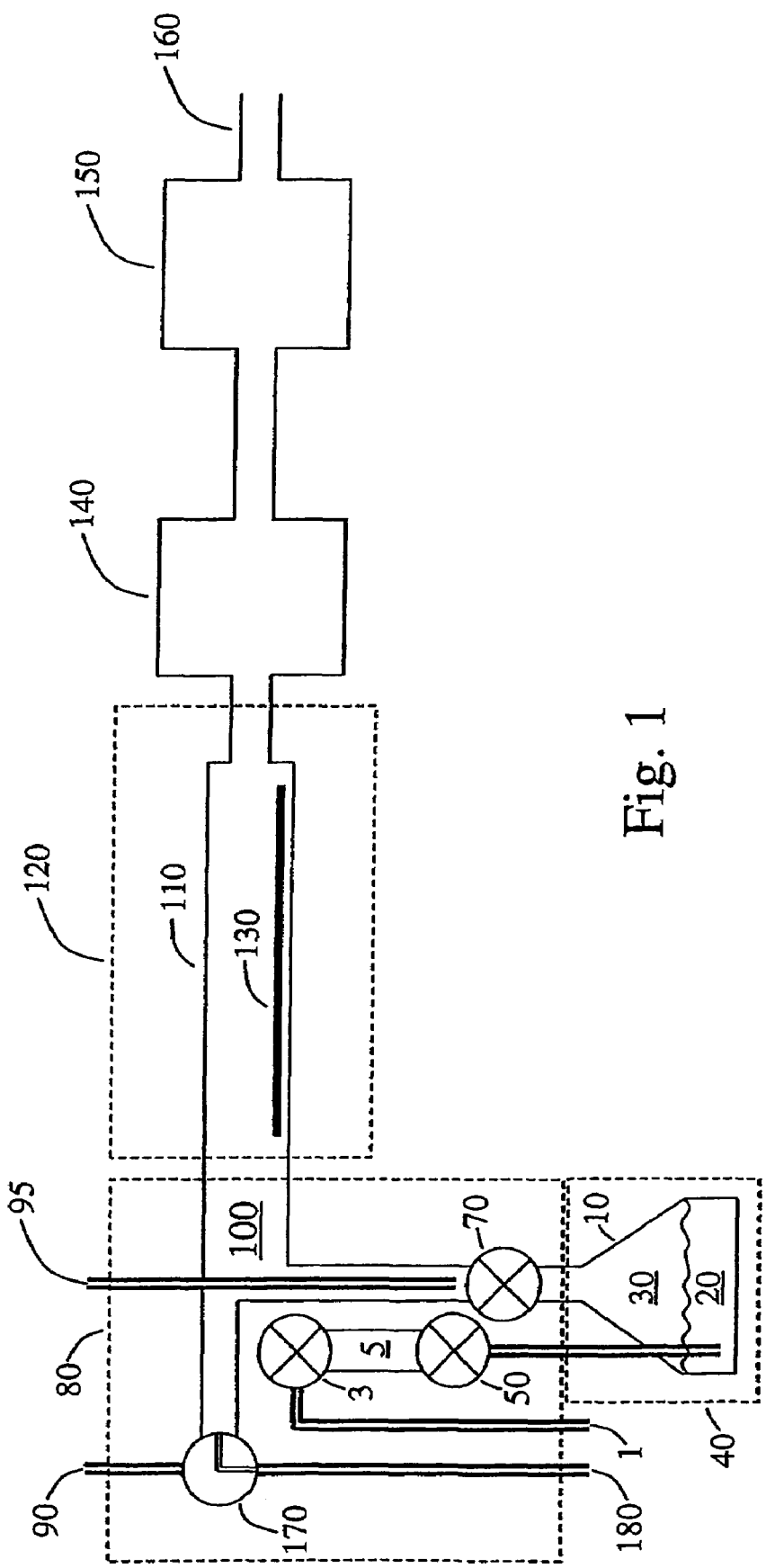
FIG. 1 is a cross-sectional illustration of an atomic deposition layer apparatus used in the practice of at least one embodiment of the invention.

1. Summary of Processes for ALD of Tungsten Nitride.

The present invention provides a method for preparing materials comprising tungsten and nitrogen, which we will refer to as "tungsten nitride" even if it contains smaller amounts of other elements such as carbon, oxygen or hydrogen. In a conventional chemical vapor deposition (CVD) method, a vapor of a tungsten precursor is reacted with a Lewis base such as ammonia on the surface of a substrate. The tungsten nitride may be formed as a film on a heated substrate. In an alternating layer deposition (ALD) process, a substrate is alternately exposed to the vapor of a tungsten precursor and then to ammonia or to another Lewis base, such as pyridine. In a plasma-assisted ALD process, a substrate is alternately exposed to the vapor of a tungsten precursor and then to a hydrogen-containing plasma. As is discussed in greater detail below, the ALD method provides highly conformal films and is suitable for use in a wide range of reaction conditions and reactant reactivity.

2. Synthesis of Tungsten Precursors.

An exemplary tungsten precursor, bis(tert-butylimido)bis(dimethylamido) tungsten(VI), $(t\text{-BuN})_2(Me_2N)_2W$, can be synthesized according to the following reaction sequence:

$WCl_6 + 4HN(t\text{-Bu})SiMe_3 => (t\text{-BuN})_2WCl_2NH_2(t\text{-Bu}) + 3\ Me_3SiCl + (t\text{-Bu})(Me_3Si)NH_2Cl$ (1)

$(t\text{-BuN})_2WCl_2NH_2(t\text{-Bu}) + 2pyr => (t\text{-BuN})_2WCl_2(pyr)_2 + (t\text{-Bu})NH_2$ (2)

$(t\text{-BUN})_2WCl_2(pyr)_2 + 2LiNMe_2 => (t\text{-BuN})_2(Me_2N)_2W + 2\ LiCl + 2pyr$ (3)

In these formulas, "t-Bu" stands for tertiary-butyl and "pyr" stands for pyridine.

As would be appreciated by one of ordinary skill in the art, other similar tungsten precursors may be prepared by similar reactions, by substituting other amines for tert-butyltimethylsilylamine and other lithium alkylamides for lithium dimethylamide. The tungsten precursors generally react with moisture in the ambient air, and should be stored under an inert, dry atmosphere such as pure nitrogen gas.

3. Detailed Description of ALD Process.

The process according to one or more embodiments of the invention may be carried out using an atomic layer deposition (ALD) apparatus. Alternating doses of first and second reactant vapors are introduced into the deposition chamber to form a layer of controlled composition and thickness on a substrate. The apparatus introduces a metered amount of a first reactant vapor into a deposition chamber having a substrate therein to be coated. A thin layer of the first reactant is deposited on the substrate. After a preselected time period, a metered amount of a second reactant vapor is then introduced into the deposition chamber and allowed to interact with the layer already deposited by the first reactant. The time period may be on the order of a few seconds and is selected to provide adequate time for the just-introduced component to react on the substrate and for any excess vapor to be removed from the headspace above the substrate. It has been determined that the surface reactions are self-limiting so that a reproducible layer of predictable composition is deposited. As will be appreciated by one of ordinary skill in the art, deposition processes utilizing more than two reactant components are within the scope of the invention.

In one embodiment of the invention, 6-port sampling valves (Valco model EP4C6WEPH, Valco Instruments, Houston, Tex.) normally used for injecting samples into gas chromatographs may be used to deliver pulses of reactant gases, liquids or solutions into a suitable carrier gas. Each time that a valve is opened, a defined volume of reactant flows into a heated tube in which liquids or solutions are vaporized. Carrier gas moves the reactant gas or vapor from the tube into the zone containing the substrate.

In another embodiment, a layer is deposited by ALD using an apparatus such as that illustrated in FIG. 1. A liquid or solid precursor 20 is placed in vessel 10 and heated by oven 40 to temperature $T_1$ at which temperature it has equilibrium vapor pressure $P_{eq}$ chosen to be less than the chamber pressure. Measured doses of tungsten precursor vapor 30 are introduced into the heated deposition chamber 110 by the use of three air-actuated diaphragm valves, 3, 50 and 70 (Titan II model made by Parker-Hannifin, Richmond, Calif.). The chamber 5 is first pressurized with carrier gas delivered through tube 1 and valve 3 from a pressure controller (not shown). Valve 3 is then closed and valve 50 opened to allow the carrier gas to pressurize precursor reservoir 10 to pressure $P_{tot}$, which pressure is chosen to be larger than the chamber pressure $P_{dep}$, and then valve 50 is closed.

The mole fraction of precursor vapor in the vapor space 30 of reservoir 10 then becomes $P_{eq}/P_{tot}$. Valve 70 is then opened in order to let a dose of the precursor vapor and carrier gas flow into the reaction zone. The number of moles delivered in this dose can be estimated from the equation $$n = (P_{eq}/P_{tot})(P_{dep})(V/RT_1),$$

where V is the volume of the vapor space 30 in chamber 10. If some carrier gas from tube 95 enters the volume 30 during the time that the valve 70 is open, then a dose somewhat larger than this estimate may be delivered. By making the volume V large enough, a precursor dose may be made large enough to cause the surface reactions to go to completion (also called "saturation"). If the vapor pressure $P_{eq}$ is so low that the required volume V would be impracticably large, then additional doses from volume V may be delivered before delivering a dose of the other reactant.

Carrier gas (such as nitrogen or hydrogen gas) flows at a controlled rate into inlets 90 and 95 in order to speed the flow of the reactants into the deposition chamber and the purging of reaction byproducts and un-reacted reactant vapor. A static mixer may be placed in the tubing 100 leading into the reactor to provide a more uniform concentration of the precursor vapor in the carrier gas as it enters the deposition chamber 110 heated by furnace 120 and containing one or more substrates 130. The reaction byproducts and un-reacted reactant vapors may be removed by trap 140 before passing into a vacuum pump 150. Carrier gas exits from exhaust 160.

Gaseous reactants, such as ammonia or hydrogen, are introduced into the tube 180 from a source tank and a pressure regulator and/or flow controller (not shown). The gas flows through 3-way valve 170 into the mixing zone 100 and then over the substrate 130 inside chamber 110 in heated zone 120. When a sufficient dose has been delivered, the 3-way valve 170 is turned into its other position so that carrier gas flows from mass-flow controller 90 into the deposition chamber 110, sweeping away any excess reactant vapor. The size of the dose is controlled by the length of time during which the 3-way valve 170 is held in the delivery position.

In an isothermal deposition zone 110, material is generally deposited on all surfaces exposed to the precursor vapors, including substrates and the interior chamber walls. Thus it is appropriate to report the precursor doses used in terms of moles divided by the total area of the substrates and exposed chamber walls. In some cases, deposition also occurs on part or all of the back side of the substrates, in which case that area should also be included in the total area.

The invention may be understood with reference to the following examples which are presented for the purpose of illustration only and which are not limiting of the invention, the full scope of which is set forth in the claims which follow.

EXAMPLE 1

Synthesis of bis(tert-butylimido)bis(dimethylamido) tungsten(VI), $(t\text{-BuN})_2(Me_2N)_2W$ 1) To a purple suspension of $WCl_6$ (30.0 g, 75.6 mmol) in toluene (300 mL) a solution of $HN(t\text{-Bu})SiMe_3$ (50 g, 344 mmol) in toluene (65 mL) was added dropwise over a period of 2 h. The suspension was stirred for a total of 24 h. The dark green suspension was filtered through Celite to remove the solid (t-Bu)(Me₃Si)NH₂Cl and any unreacted WCl₆. The dark brown filtrate was dried under vacuum in a warm water bath. 50 mL of hexane was added to the resulting dark brown solid and stirred in order to dissolve some impurities. The brown suspension was cooled in the freezer for overnight, and then the dark brown supernatant solution containing the impurities was decanted. NMR for [(t-BuN)$_2$WCl$_2$ NH$_2$(t-Bu)]$_2$ $^1$H NMR (CDCl$_3$): δ 4.3 (br, 4, H$_2$NMe$_3$), 1.45(s, 18, μ-NCMe$_3$), 1.40(s, 18, NCMe$_3$), 1.33(s, 18, H$_2$NCMe$_3$). (Reference for this first reaction: A. J. Nielson, *Polyhedron*, volume 6, page 1657, 1987)

2) The solid product from the first step was suspended in 200 mL of ether. To this yellowish brown suspension excess pyridine (30 mL, 371 mmol) was added. The suspension turned black immediately. The suspension was stirred for 30 min and then placed under vacuum to remove ether, tert-butylamine and excess pyridine, leaving a black solid. NMR for (t-BuN)$_2$WCl$_2$ (pyr)$_2$ $^1$H NMR (CDCl$_3$): δ 8.93 (m, 4, o-py) 7.62 (m, 2, p-py), 7.42 (m, 4, m-py) 1.40 (s, 18, NCMe$_3$). (Reference for this second reaction: J. Sundermeyer, *Chem. Ber.*, volume 124, page 1977, 1991.)

3) 300 mL of ether was added to the solid, and then LiNMe$_2$ (12.0 g, 235.2 mmole) was added very slowly to the suspension. (Caution! The reaction is very vigorous and exothermic.) The addition of the lithium dimethylamide can be carried out from a solid addition funnel through a reflux column. The resulting brown suspension was stirred overnight and then dried under vacuum to remove ether and pyridine. The sticky black residue was extracted with portions of hexanes (total 300 mL) and filtered over Celite to remove LiCl and excess LiNMe$_2$. The black filtrate was dried under vacuum, and then the black residue was distilled twice under reduced pressure (bp. 77-78° C. at 23 mTorr) to afford the product as a pale yellow liquid (12.3 g, yield 39%). $^1$H NMR (C$_6$D$_6$): δ 3.50 (s, 12, NMe$_2$), 1.40 (s, 18, NCMe$_3$). $^{13}$C{$^1$H} NMR (C$_6$D$_6$): 66.4 (2, NCMe$_3$), 53.8 (4, NMe$_2$), 34.1 (6, NCMe$_3$). Elemental composition for C$_{12}$H$_{30}$N$_4$W, found (calculated): 35.07 (34.79)% C, 7.22 (7.30)% H, 13.14 (13.53)% N, (44.38)% W.

EXAMPLE 2

Synthesis of bis(tert-butylimido)bis(ethylmethylamido)tungsten(VI)

To synthesize bis(tert-butylimido)bis(ethylmethylamido) tungsten(VI), (t-BuN)$_2$(EtMeN)$_2$W, the LiNMe$_2$ is replaced with LiNEtMe. The product is a pale yellow liquid (17.1 g, yield: 50%)(bp 79-81° C. at 20 mTorr). $^1$H NMR (C$_6$D$_6$): δ 3.70 (q, 4, $^3$J=7.0 Hz, N(CH$_2$CH$_3$)Me), 3.50 (s, 12, NEtMe), 1.40 (s, 18, NCMe$_3$), 1.18 (t, 6, $^3$J=7.0 Hz, N(CH$_2$CH$_3$)Me). $^{13}$C{$^1$H} NMR (C$_6$D$_6$): 66.2 (2, NCMe$_3$), 59.7 (2, N(CH$_2$CH$_3$)Me), 50.1 (2, NEtMe), 34.0 (6, NCMe$_3$), 16.3 (2, N(CH$_2$CH$_3$)Me). Elemental composition for C$_{14}$H$_{34}$N$_4$W, found (calculated): 37.74 (38.01)% C, 7.90 (7.75)% H, 12.51 (12.67)% N, (41.57)% W.

EXAMPLE 3

ALD of Tungsten Nitride

The apparatus of FIG. 1 was used to deposit tungsten nitride coatings. Bis(tert-butylimido)bis(dimethylamido) tungsten (VI) was placed in a stainless steel container 10 having vapor volume of 0.6 liter and heated to 30° C., at which temperature the tungsten precursor has a vapor pressure of about 6 milliTorr. Ammonia was held in a compressed gas cylinder at 20° C., and passed through a pressure regulator so that its pressure was reduced to 2.4 atmospheres. A silicon substrate 130 was prepared by dissolving its native oxide by placing it in dilute hydrofluoric acid solution for a few seconds. Next the substrate was irradiated by ultraviolet light (e.g. UV mercury lamp) in air until the surface became hydrophilic (about 3 minutes). Then the substrate 130 was placed on a half-round substrate holder 25 cm long in chamber 110 having diameter 2.4 cm and heated over a length 30 cm to a temperature of 300° C. Another silicon substrate with narrow holes (0.1 microns by 0.2 microns wide and 7.3 microns deep) was also cleaned and placed in the chamber 110.

Using the apparatus of FIG. 1, the deposition cycle began by introducing nitrogen at 0.5 atmosphere pressure into the gas volume 5 containing 12 cm$^3$. After pressurizing volume 30 with this nitrogen, opening valve 70 for 1 second released a dose of about 4×10$^{-10}$ moles/cm$^2$ of the tungsten precursor vapor into the deposition chamber 110. A vacuum pump moved the tungsten precursor through the chamber in about 20 milliseconds. Then nitrogen flowed for 10 seconds to purge the chamber of excess tungsten precursor as well as volatile byproducts of the reaction. The carrier gas also flowed through valve 170 during this tungsten vapor dose and purge step. To deliver a pulse of ammonia gas, the three-way valve 170 with inner channels 0.4 mm inner diameter, was opened to ammonia for 1 second, during which time about 5×10$^{-6}$ moles/cm$^2$ of ammonia flowed into the deposition chamber. Then the three-way valve 170 was turned to allow the flow of nitrogen carrier gas for 10 seconds to purge the chamber of residual ammonia gas. This cycle was then repeated 999 more times.

After these 1000 cycles were completed, the substrate 130 was removed from the reactor. The substrate was examined by scanning electron microscopy and found to have a film of tungsten nitride with a uniform thickness of 50 nm along the length of the deposition zone. Each of the cycles deposited about 0.05 nm of film. Rutherford Backscattering was used to determine the chemical composition of the film to be WN$_{1.1\pm0.1}$. The density of the films was measured to be about 12 g/cm$^2$.

The film developed according to the foregoing possessed very desirable, smooth surface characteristics. Atomic force microscopy confirmed that the surface roughness of the deposited layer was very similar, if not equal to that of the substrate on which it was deposited. X-ray diffraction showed that the layer was mostly amorphous along with small amounts of extremely small crystallites shown by the presence of weak, broad diffraction peaks corresponding to the known cubic, crystalline phase of WN. This structural information was confirmed by transmission electron microscopy (TEM), which showed some crystallites up to 3 nm in size in an amorphous matrix.

Figure 2:
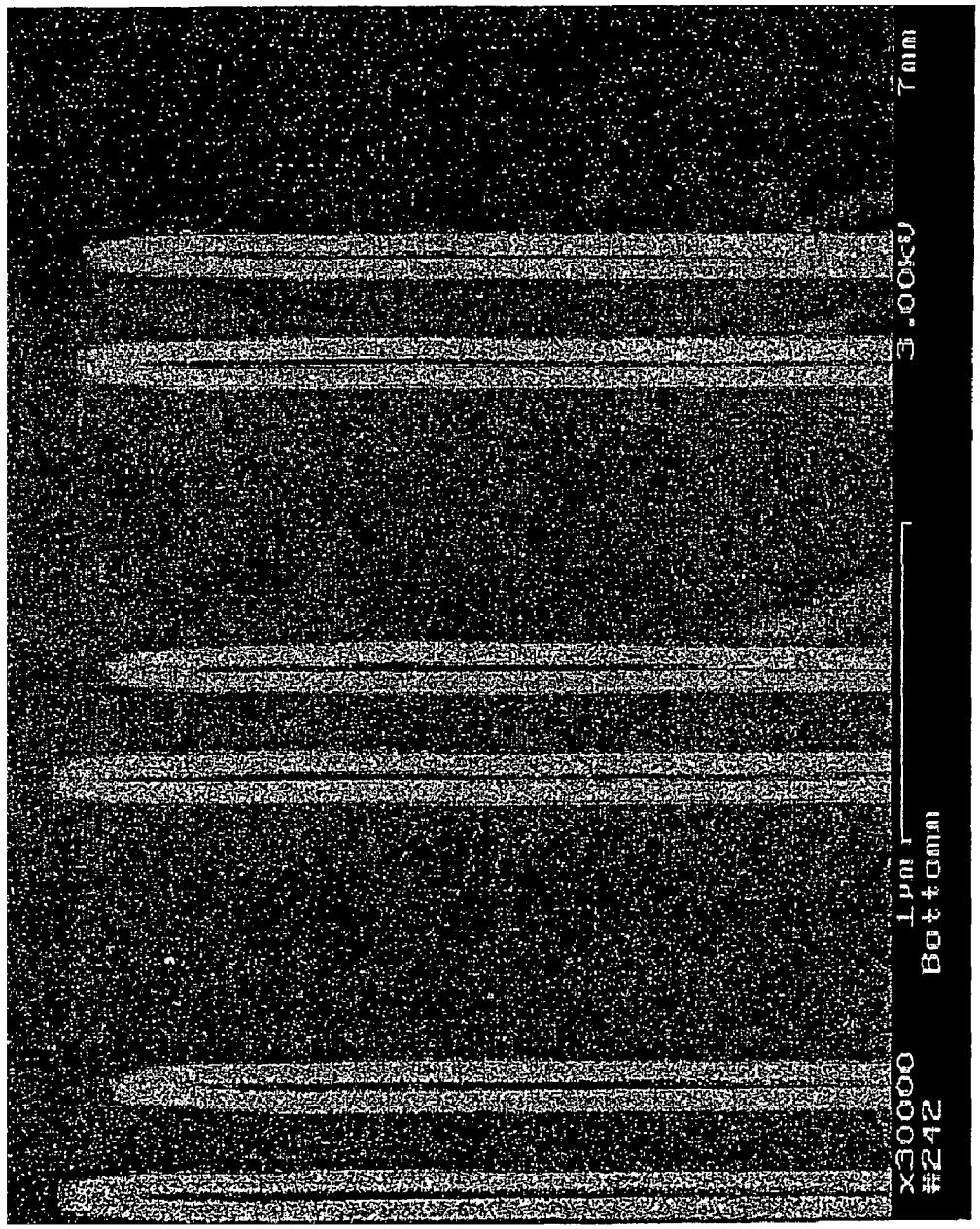
FIG. 2 is a cross-sectional scanning electron micrograph of holes in a silicon wafer uniformly coated with tungsten nitride using one embodiment of the invention.

A scanning electron micrograph (SEM) was taken of a wafer with narrow holes having aspect ratio 40:1 coated with WN$_x$ by the process described in the first paragraph of this example and then cleaved to show a cross-section of the coated holes. The SEM in FIG. 2 shows that the walls of the narrow hole are covered with a perfectly conformal coating. In other similar samples, good step coverage for holes having aspect ratios of over 200:1 were observed. These results demonstrate the excellent step coverage achieved by the process of the invention.

The electrical resistivity of the tungsten nitride coating is about 1.5×10$^{-3}$ ohm-cm. The resistivity was reduced to less than 4×10$^{-4}$ ohm-cm by annealing in forming gas at 800° C. for 30 minutes. The annealed film had crystallized to the cubic tungsten structure and lost its nitrogen to become pure tungsten metal.

EXAMPLE 4

Example 3 was repeated, except that the tungsten nitride film was deposited directly on silicon without an oxide interlayer produced by the UV-ozone treatment. Annealing the $WN_x$ to a temperature of 1000° C. produced a coating of tungsten silicide.

EXAMPLE 5

Example 3 was repeated, except that the exposure time to tungsten precursor vapor was increased from 10 seconds to 60 seconds. Identical results were obtained, showing that the chemical reactions of the tungsten precursor were completed within 10 seconds.

EXAMPLE 6

Example 3 was repeated, except that the sizes of the tungsten doses were doubled. The film thickness and its properties were unchanged from those of Example 3. These results show that the surface reactions of the tungsten precursor are self-limiting.

EXAMPLE 7

Example 3 was repeated, except that the sizes of the ammonia doses were doubled. The film thickness and its properties were unchanged from those of Example 3. These results show that the surface reactions of the ammonia are self-limiting.

EXAMPLE 8

Figure 3:
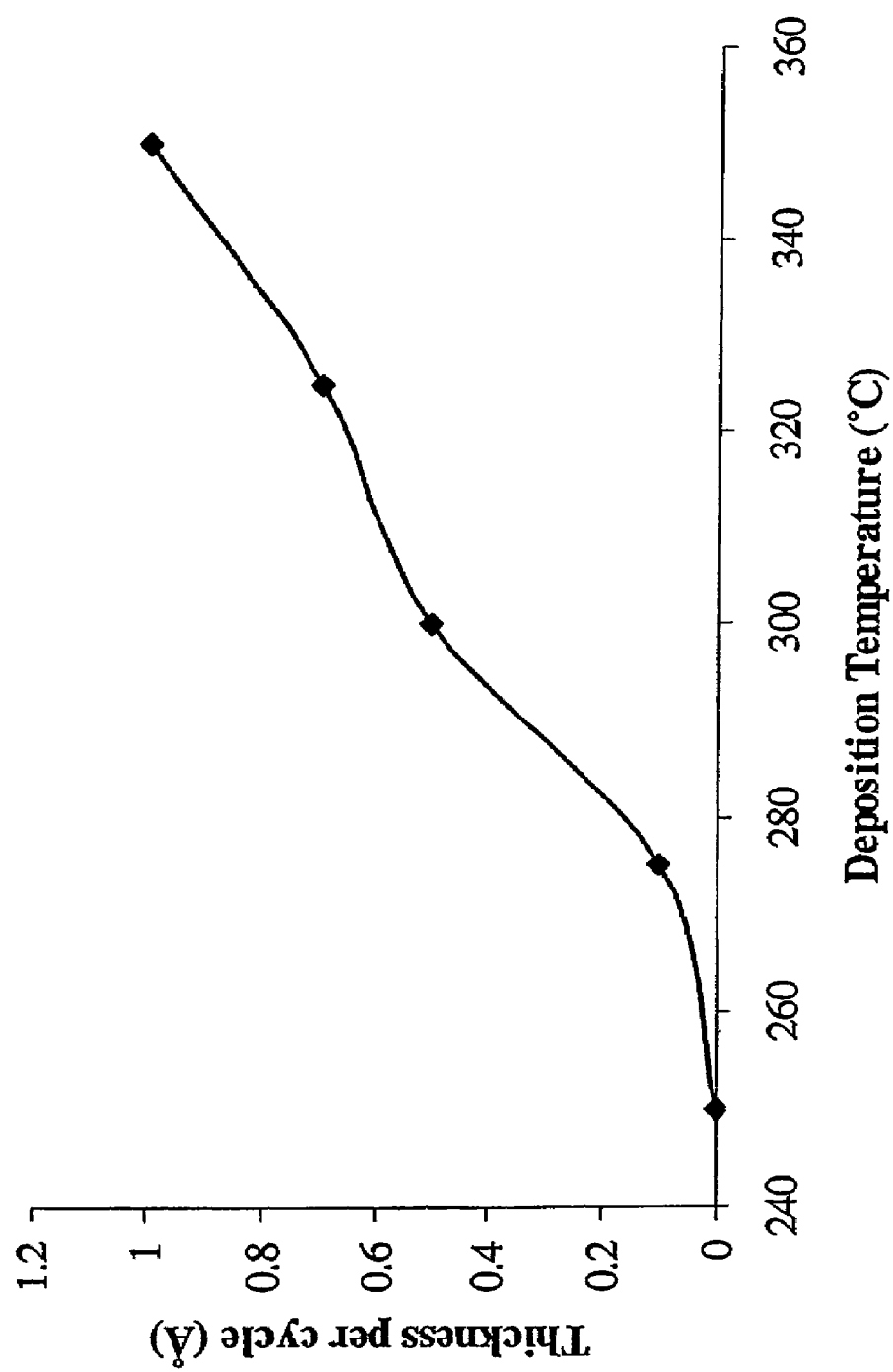
FIG. 3 is a graphical representation illustrating that the thickness of the layer deposited per cycle depends on the temperature of the substrate during deposition.

Example 3 was repeated, except that the substrate temperatures were varied within the range from 250° C. to 350° C. Similar tungsten nitride films were obtained, except that the thicknesses of the films varied with the substrate temperature as shown in FIG. 3. No films were formed at temperatures below 250° C. Films formed at temperatures above 350° C., but they contained carbon in addition to tungsten and nitrogen, and their step coverage was not as good as for the films made in the range 250° C. to 350° C.

EXAMPLE 9

Example 3 was repeated with hydrogen plasma in place of the ammonia. 250 Watts of RF power (13.56 MHz) was capacitatively coupled to form the hydrogen plasma. Similar results that those of Example 3 were obtained, except that the resistivity of the as-deposited film was much lower, about $4 \times 10^{-4}$ ohm-cm, and the carbon content was higher.

EXAMPLE 10

Example 3 was repeated using substrates of fused silica, quartz, soda-lime glass, glassy carbon, stainless steel, aluminum, copper and gold. Identical results were obtained.

Comparative Example 1

Example 1 was repeated using only the tungsten precursor and no ammonia No film was deposited.

EXAMPLE 11

The ALD tungsten nitride films were shown to be good barriers to the diffusion of copper by the following tests. 100 nm of copper was sputtered on top of various films of tungsten nitride ranging in thickness from 1 nm to 100 nm on silicon substrates, including films with thicknesses of 1 nm, 2 nm, 5 nm, 10 nm, 20 nM, 50 nm and 100 nm. Samples of these Si/WN/Cu structures were annealed in forming gas for 30 minutes at various temperatures. The copper on the surface was dissolved in nitric acid solution, and then the tungsten nitride was dissolved in ammonia/hydrogen peroxide solution. Examination of the silicon by SEM showed no change in samples annealed at 450, 500 or 550° C. A sample annealed at 600° C. showed a few bright crystals of copper silicide due to isolated breakdown of the tungsten nitride barrier. A sample annealed at 650° C. showed numerous crystals of copper silicide due to complete breakdown of the barrier. These results are conventionally interpreted to mean that the tungsten nitride is stable to 550° C. and is an excellent barrier to diffusion of copper, even for films only about 1 nm or 2 nm thick.

EXAMPLE 12

Copper oxide was deposited on tungsten nitride films by ALD from 100 cycles of alternating exposure to copper(II) bis(sec-butylacetoacetate) vapor and an ozone/oxygen gas mixture at a substrate temperature of 200° C. using an apparatus described by FIG. 1 with the copper precursor in chamber 10 and the ozone/oxygen mixture from an ozone generator passing into tube 180. Copper oxide, CuO, was deposited at a rate of about 0.05 nm per cycle. The copper oxide was reduced to copper metal by heating the sample to 500° C. in a hydrogen atmosphere for 1 hour. The resulting shiny copper layer adhered strongly to the tungsten nitride, and could not be removed by adhesive tape.

EXAMPLE 13

The thin ALD copper layer produced in Example 12 can be used as a "seed" layer to initiate the CVD of copper using the process described by E. S. Hwang and J. Lee in Chemistry of Materials, volume 12, page 2076, 2000.

EXAMPLE 14

The thin ALD copper layer produced in Example 12 can be used as a "seed" layer to initiate the electrochemical plating of copper by well-known methods.

EXAMPLE 15

The A/D process of the invention can be used to make a capacitor having the structure $WN_x/HfO_2/WN_x$, in which the $WN_x$ layers are the electrically conducting electrodes and the $HfO_2$ is the insulating dielectric layer. The $HfO_2$ can be made by ALD reaction of tetrakis(dimethylamido)hafnium and water vapor as described in Example 12 of WO 0227063.

EXAMPLE 16

The ALD process of the invention can be used to make a capacitor having the structure $WN_x/Ta_2O_5/WN_x$, in which the $WN_x$ layers are the electrically conducting electrodes and the $Ta_2O_5$ is the insulating dielectric layer. The $Ta_2O_5$ can be made by ALD reaction of ethylimidotris(diethylamido)tantalum and water vapor as described in Example 15 of WO 0227063.

EXAMPLE 17

Example 3 was repeated, using isotopically labeled $^{15}NH_3$ in place of the normal $^{14}NH_3$. The tungsten nitride film was analyzed by Rutherford Backscattering, which showed that the nitrogen in the film is normal nitrogen $^{14}$N, not $^{15}$N. Thus the nitrogen in the film arises from the nitrogen in the tungsten precursor, not from the ammonia.

EXAMPLE 18

Example 3 was repeated with pyridine vapor in place of the ammonia. Similar results were obtained. The effectiveness of pyridine in producing tungsten nitride films is consistent with the proposition that the second component of the ALD process serves to activate the deposition process, but that it itself is not incorporated into the deposited film. Pyridine cannot undergo transamination, yet it nonetheless deposits tungsten nitride films. This suggests that the second component of the ALD process acts as a base catalyst in the reaction.

Those skilled in the art will recognize or be able to ascertain using no more than routine experimentation, many equivalents to the specific embodiments of the invention described specifically herein. Such equivalents are intended to be encompassed within the scope of the following claims.

What is claimed is:

1. A compound having a formula

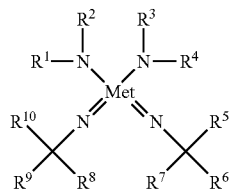

wherein Met is W or Mo, any one of R$^1$ through R$^{10}$ independently represent alkyl groups, arylalkyl groups, alkenylalkyl groups, alkynylalkyl groups, fluoroalkyl groups or alkyl groups substituted with other atoms or groups selected to enhance the volatility of the compound, where when Met is W and R$^2$ and R$^4$-R$^{10}$ are methyl, then R$^1$ and R$^3$ are not both methyl or both ethyl, and when Met is Mo and R$^5$-R$^{10}$ are methyl, R$^1$-R$^4$ are not ethyl.

2. The compound of claim 1, wherein the Met is W.

3. The compound of claim 1, wherein the Met is Mo.

4. A process for depositing a thin film on a surface of a substrate, the process comprising:
introducing a vapor of a first material comprising one or more compounds claimed in claim 1 to the substrate wherein at least a portion of the vapor of the first material adsorbs on the surface of the substrate; then
introducing a vapor of a second material wherein the second material activates the first material to react and form the thin film on the surface of the substrate.

5. The process of claim 4, further comprising:
removing at least a portion of the vapor of the first material that has not adsorbed on the substrate from the vicinity of the substrate before introducing the vapor of the second material; and
removing at least a portion of the vapor of the second material from the vicinity of the substrate.

6. The process of claim 4, wherein the thin film comprises tungsten and nitrogen.

7. The process of claim 4, wherein the first material comprises tungsten, molybdenum, or mixtures thereof.

8. The process of claim 4, wherein the first material comprises one or more compounds comprising tungsten-nitrogen bonds.

9. The process of claim 4, wherein the first material comprises one or more compounds comprising molybdenum-nitrogen bonds.

10. The process of claim 4, wherein the second material comprises a Lewis base.

11. The process of claim 10, wherein the Lewis base comprises ammonia.

12. The process of claim 10, wherein the Lewis base comprises pyridine.

13. The process of claim 4, wherein the second material comprises a hydrogen atom.

14. The process of claim 4, wherein the second material comprises at least one hydrogen atom.

15. The process of claim 4, wherein the substrate is maintained at a temperature in the range of 200° C. to 400° C.

16. A process for depositing a thin film on a surface of a substrate, the process comprising:
introducing a vapor of a first material and a vapor of a second material to the surface of the substrate; wherein the first material comprises one or more compounds claimed in claim 1.

17. The process of claim 16, wherein the Met is W.

18. The process of claim 16, wherein the second material comprises ammonia.

19. The process of claim 16, wherein the second material comprises pyridine.

20. The process of claim 16, wherein the second material comprises a hydrogen plasma.

21. The process of claim 16, wherein the second material comprises at least one hydrogen atom.

22. The process of claim 16, wherein the substrate is maintained at a temperature in the range of 200° C. to 400° C.

23. A process for depositing a material, the process comprising:
introducing a compound as claimed in claim 1 to a surface.

24. The process of claim 23, wherein the Met is W.

25. The process of claim 23, further comprising:
introducing a vapor of a second material, wherein
the compound comprises at least two elements of the deposited material; and
the deposited material is substantially free of elements of the second material.

26. The process of claim 25, wherein the second material comprises a Lewis base.

27. The process of claim 26, wherein the Lewis base comprises ammonia.

28. The process of claim 26, wherein the Lewis base comprises pyridine.

29. The process of claim 25, wherein the second material comprises a hydrogen plasma.

30. The process of claim 25, wherein the second material comprises at least one hydrogen atom.

31. The process of claim 23, wherein the substrate is maintained at a temperature in the range of 200° C. to 400° C.

* * * * *